(12) United States Patent
Veillon, Jr. et al.

(10) Patent No.: US 6,821,267 B2
(45) Date of Patent: Nov. 23, 2004

(54) LUER TIP CAP HAVING REDUCED REMOVAL FORCE

(75) Inventors: Joseph N. Veillon, Jr., McHenry, IL (US); Jennifer J. Boesch, Wheeling, IL (US); Edwin Chim, Vernon Hills, IL (US); Derek Walsh, Wonderlake, IL (US); Robert Passaglia, Arlington Heights, IL (US); Erin Lundtveit, Wadsworth, IL (US)

(73) Assignee: Baxter International, Deerfield, IL (US)

( * ) Notice: Subject to any disclaimer, the term of this patent is extended or adjusted under 35 U.S.C. 154(b) by 57 days.

(21) Appl. No.: 10/092,738

(22) Filed: Mar. 7, 2002

(65) Prior Publication Data

US 2003/0171719 A1 Sep. 11, 2003

(51) Int. Cl.[7] .............................................. A61M 5/32
(52) U.S. Cl. ..................... 604/192; 604/263; 215/355; 220/796; 222/562; 222/544
(58) Field of Search ................. 604/110, 111, 604/192, 256, 197–199, 246, 265, 905, 403; 215/329, 355; 220/780, 784, 787, 789, 796, 799–801; 222/562, 563, 544–547; 141/18; 206/571, 364

(56) References Cited

U.S. PATENT DOCUMENTS

| | | | |
|---|---|---|---|
| 4,202,334 A | | 5/1980 | Elson |
| 4,465,472 A | * | 8/1984 | Urbaniak ..................... 604/122 |
| 4,616,760 A | | 10/1986 | Kersten et al. |
| 4,735,311 A | | 4/1988 | Lowe et al. |
| 4,753,345 A | * | 6/1988 | Goodsir et al. ............. 206/366 |
| 4,779,997 A | | 10/1988 | Schmidt |
| 4,836,397 A | | 6/1989 | Fowles |
| 4,889,256 A | | 12/1989 | Fowles |
| 4,892,222 A | | 1/1990 | Schmidt et al. |
| 4,903,855 A | | 2/1990 | Ducay et al. |
| 4,998,922 A | | 3/1991 | Kuracina et al. |
| 5,088,995 A | | 2/1992 | Packard et al. |
| 5,092,852 A | | 3/1992 | Poling |
| 5,197,953 A | | 3/1993 | Colonna |
| 5,385,253 A | | 1/1995 | Scharf et al. |
| 5,607,400 A | | 3/1997 | Thibault et al. |
| 5,610,253 A | | 3/1997 | Hatke et al. |
| 5,741,236 A | * | 4/1998 | Kakiuti ...................... 604/192 |
| 5,785,691 A | | 7/1998 | Vetter et al. |
| 5,855,230 A | | 1/1999 | Guala et al. |
| 6,004,299 A | * | 12/1999 | Arai et al. .................. 604/218 |
| 6,065,270 A | | 5/2000 | Reinhard et al. |
| 6,190,364 B1 | | 2/2001 | Imbert |
| 6,196,998 B1 | | 3/2001 | Jansen et al. |
| 6,280,418 B1 | * | 8/2001 | Reinhard et al. ........... 604/187 |
| 6,344,034 B1 | * | 2/2002 | Sudo et al. ................. 604/263 |
| 6,361,524 B1 | * | 3/2002 | Odell et al. ................. 604/187 |
| 6,491,665 B1 | * | 12/2002 | Vetter et al. ................ 604/181 |
| 6,503,230 B2 | * | 1/2003 | Odell et al. ................. 604/263 |
| 6,520,935 B1 | * | 2/2003 | Jansen et al. ............... 604/111 |
| 6,585,691 B1 | * | 7/2003 | Vitello ........................ 604/111 |

FOREIGN PATENT DOCUMENTS

| | | |
|---|---|---|
| DE | 29505787 | 6/1995 |
| EP | 0098411 B2 | 6/1983 |

* cited by examiner

Primary Examiner—Brian L. Casler
Assistant Examiner—Cris L. Rodriguez
(74) Attorney, Agent, or Firm—Jeffrey C. Nichols

(57) ABSTRACT

A tip cap for a luer of a polymeric medical solution container. The tip cap has an integral body having an outer portion and a cavity extending to an inner portion. The cavity has a frustoconical inner surface and an annular ring extending from the inner surface radially toward a centerline of the tip cap.

24 Claims, 2 Drawing Sheets

LUER TIP CAP HAVING REDUCED REMOVAL FORCE

DESCRIPTION

1. Technical Field

The present invention relates generally to a cap for luer of a medical container, and more specifically to a tip cap for a syringe luer interface that reduces the removal force of the cap from the syringe luer interface.

2. Background Prior Art

Syringe bodies have been typically manufactured of glass. The glass syringe bodies are initially manufactured in a production plant. The syringe bodies are then packaged and shipped to a pharmaceutical plant where they are unpackaged, filled, sealed tightly, and sterilized. Finally, the syringe bodies are repackaged and ready to be delivered to the end user. This process is inefficient and costly.

Recently, syringe bodies have been manufactured from polymeric resins. The polymeric syringe bodies replaced the glass syringe bodies which were costly to produce and caused difficulties during the manufacturing process because the glass would chip, crack, or break. The broken glass particles would not only become hazards to workers and manufacturing equipment, but could also become sealed within the glass syringe body causing a potential health hazard to a downstream patient.

U.S. Pat. No. 6,065,270 (the '270 patent), issued to Reinhard et al. and assigned to Schott Glaswerke of Germany, describes a method of producing a prefilled, sterile syringe body from a cyclic olefin copolymer (COC) resin. A COC polymer is useful in the manufacture of syringe bodies because it is generally clear and transparent. COC resins are, for example, disclosed in U.S. Pat. No. 5,610,253 which is issued to Hatke et al. and assigned to Hoechst Akteiengesellschaft of Germany.

The '270 patent includes a method of manufacturing a filled plastic syringe body for medical purposes. The syringe body comprises a barrel having a rear end which is open and an outlet end with a head molded thereon and designed to accommodate an injection element, a plunger stopper for insertion into the rear end of the barrel to seal it, and an element for sealing the head. The method of manufacturing the syringe body includes the steps of: (1) forming the syringe body by injection molding a material into a core in a cavity of an injection mold, the mold having shape and preset inside dimensions; (2) opening the mold and removing the formed syringe body, said body having an initial temperature; (3) sealing one end of the barrel of the plastic syringe body; (4) siliconizing an inside wall surface of the barrel of the plastic syringe body immediately after the body is formed and while the body remains substantially at said initial temperature; (5) filling the plastic syringe body through the other end of the barrel of the plastic syringe body; and (6) sealing the other end of the barrel of the plastic syringe body, wherein the method is carried out in a controlled environment within a single continuous manufacturing line. According to the method of the '270 patent, the sterilization step is applied to the filled and completely sealed ready-to-use syringe body. Historically, sterilization of finished syringe components (barrel, plunger, and tip cap) has been conducted using ethylene oxide, moist-heat or gamma irradiation.

The luer tip of the syringe body typically includes a stopper mounted over the tip at the distal end of the syringe barrel to prevent leakage of the contents of the syringe body and to avoid contamination therein. Typically, the stopper comprises a tip cap that provides a positive sealing engagement mechanism for the luer tip of the syringe body.

Generally, the tip of the syringe body has an exterior geometry having a sloped outer wall. Accordingly, prior art tip caps are generally manufactured with an interior cavity having a reverse sloped inner wall that mates with the sloped outer wall of the tip of the syringe body (See FIG. 1). Typically, the sloping inner diameter of the cavity of the tip cap is slightly smaller than the sloping outer diameter of the outer wall of the tip of the syringe body to provide a line-type interference fit. Specifically, at the distal end of the tip of one typical syringe body the outer diameter is 4.0 mm, and the mating interior diameter of the corresponding prior art tip cap shown in FIG. 1 is 3.4 mm. This line-type of interference fit is provided to produce the positive sealing engagement thought to be desired between the tip cap and the syringe tip in the prior art devices. However, because of the geometry of the mating syringe tip and tip cap, during removal the Poisson Ration effect occurs. This lateral contraction, in addition to the line-type interference fit sometimes resulted in undesirable contact and removal forces. Additionally, in extreme cases, the increased contact and removal forces due to the line-type interference fit led to failure of the tip cap adjacent the internal protrusion thereof.

Other types of tip caps for syringes are known in the art. U.S. Pat. No. 6,190,364 (the '364 patent), issued to Imbert and assigned to Becton, Dickson and Company, describes another prior art tip cap for securely sealing the tip of a hypodermic syringe barrel. As shown in FIG. 1 of the '364 patent, referenced as FIG. 2 wherein, the tip cap 154 of the '364 patent comprises two components: an inner cap 156 and an outer cap 158. The inner cap 156 is manufactured of an elastomeric material and frictionally and/or resiliently engages portions of the syringe tip for sealing the passage through the tip. The outer cap 158 is manufactured of a rigid material which protectively encloses the inner cap. The tip cap 154 of the '364 patent does not itself engage and secure the tip of the syringe barrel, but rather additionally requires a separate mounting collar 144. Thus, the mounting collar 144 engages the syringe tip and is also adapted to have the tip cap 154 secured thereto.

SUMMARY OF THE INVENTION

The present invention provides a tip cap with a reduced removal force when being removed from a luer tip. The tip cap comprising a body having an outer surface, a proximal end, a distal end, and an inner surface extending into the body at the proximal end to define a cavity. An annular ridge extends radially into the cavity from the inner surface of the body. When connected to the luer tip, the annular ridge defines a contact area to engage the luer tip, as well as a seal area between the tip cap and the luer tip. Additionally, the contact area of the annular ridge decreases the surface area of contact between the tip cap and the luer tip.

According to another aspect of the present invention, a plurality of annular ridges extend radially into the cavity from the inner surface of the body.

According to another aspect of the present invention, the body of the tip cap, including the annular ridges, is a unitary element that is made as a single component.

According to another aspect of the present invention, a removable tip cap is provided for a luer of a polymeric medical solution container. The tip cap has an integral body having an outer portion and a cavity extending to an inner portion. The cavity has a frustoconical inner surface and an annular ring extending from the inner surface radially toward a centerline of the tip cap. A protrusion is provided at a distal end of the cavity and is adapted to extend into a passage in the luer.

According to another aspect of the present invention, the cavity has a proximal end and a distal end. A diameter of the proximal end of the cavity is larger than a diameter of the distal end of the cavity, a diameter of the distal end of the cavity is larger than a diameter at the end of the luer, and a diameter of the proximal end of the cavity is larger than a diameter of the luer.

According to another aspect of the present invention, a removable tip cap is provided for an elongated luer tip projecting from a distal end of a fluid chamber. The tip cap has an integral body having an outer surface, a proximal end, a distal end, and a cavity extending into the body at the proximal end thereof. The tip cap further has an inner surface having a plurality of adjacent annular ridges extending radially toward a centerline of the body to define the cavity. The plurality of annular ridges defines contact areas adapted to engage the luer tip. The contact areas decrease the area of contact area between the tip cap and the luer tip, and create annular seals with the luer tip. Each of the plurality of annular ridges defines an independent seal area with the luer tip.

According to another aspect of the present invention, a removable tip cap is provided for a luer of a polymeric medical solution container. The tip cap has an integral body having an outer portion and a cavity extending adjacent a proximal end of the body to an inner portion thereof. The cavity further has a frustoconical inner surface and a plurality of annular rings extending from the inner surface radially toward a centerline of the tip cap. As such, the tip cap is adapted to removably engage the luer of the solution container.

According to another aspect of the present invention, a portion of the frustoconical inner surface of the tip cap has a surface contact area less than a surface contact area of the luer.

According to another aspect of the present invention, the annular rings provide an interference fit for securing the tip cap on the luer. Additionally, the annular rings provide for an incremental removal force during removal of the tip cap from the luer.

According to yet another aspect of the present invention, a removable tip cap is provided for a luer of a syringe. The tip cap has an integral body having an outer portion and a frustoconical cavity extending to an inner portion, and a plurality of annular ridges extending into the cavity and defining annular contact areas engaging the luer of the syringe. The annular contact areas correspond to annular areas having increased contact pressures which decreases the contact pressure between the tip cap and the luer adjacent the distal portion of the tip cap. Furthermore, the annular contact areas result in incremental removal forces due to elongation of the tip cap during removal of the tip cap from the luer.

Other features and advantages of the invention will be apparent from the following specification taken in conjunction with the following drawings.

BRIEF DESCRIPTION OF THE DRAWING

To understand the present invention, it will now be described by way of example, with reference to the accompanying drawings in which.

DETAILED DESCRIPTION OF THE INVENTION

Figure 1:
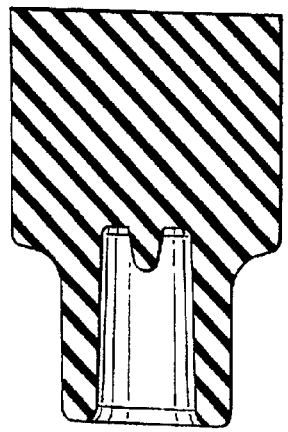
FIG. 1 is a side perspective view of a prior art tip cap for a syringe.
Figure 2:
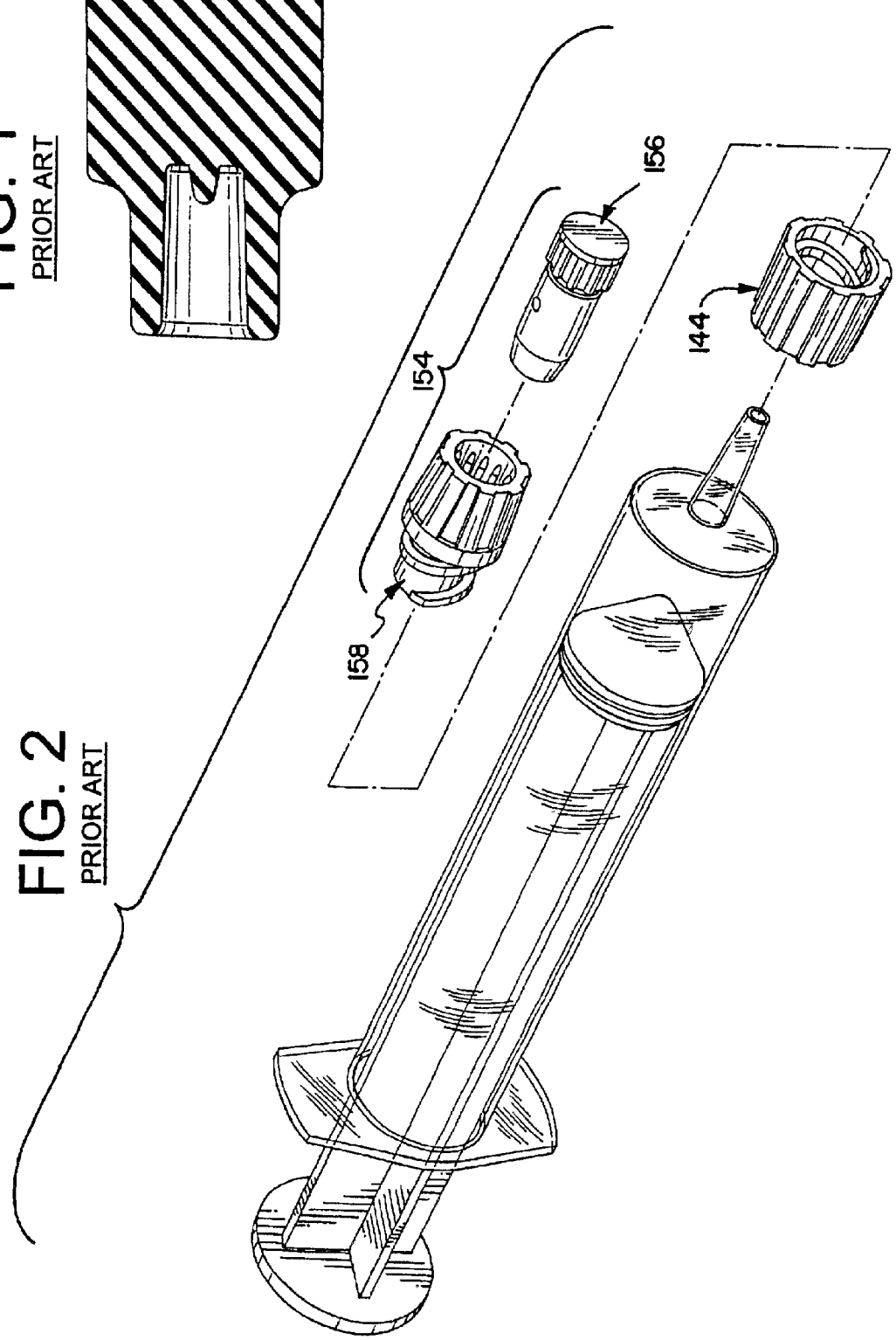
FIG. 2 is a prior art tip cap disclosed in U.S. Pat. No. 6,190,364.

While this invention is susceptible of embodiments in many different forms, there are shown in the drawings and will herein be described in detail, preferred embodiments of the invention with the understanding that the present disclosures are to be considered as exemplifications of the principles of the invention and are not intended to limit the broad aspects of the invention to the embodiments illustrated.

Figure 3:
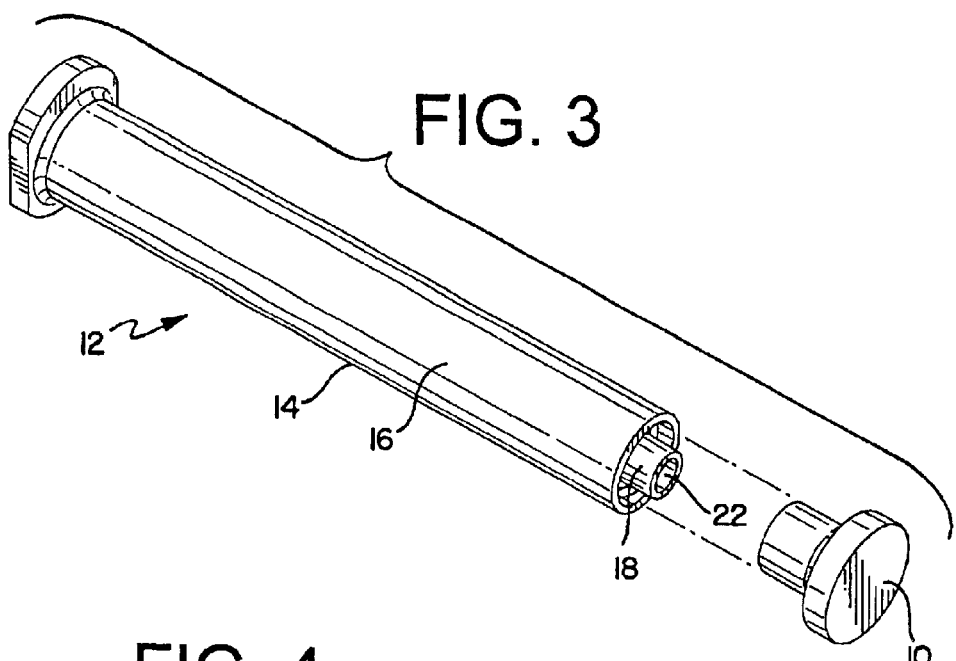
FIG. 3 is a perspective view of a syringe body with a tip cap of the present invention.
Figure 4:
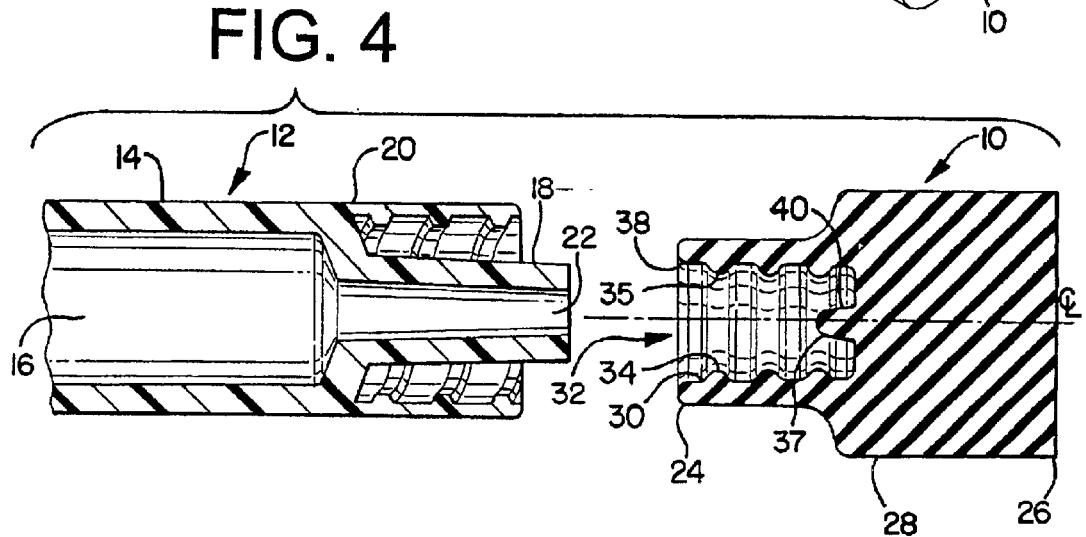
FIG. 4 is an exploded side cross-sectional view of the tip cap and the syringe body of the present invention; and, FIG. 5 is a side cross-sectional view of the tip cap connected to the syringe body of FIG. 4.
Figure 5:
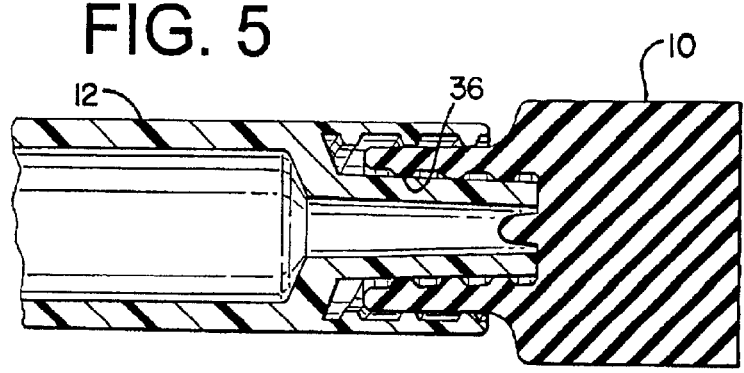

Referring now in detail to the Figures, and initially to FIGS. 3–5, there is shown a tip cap 10, constructed in accordance with the teachings of the present invention, for a solution container. Typically, the solution container will be a syringe 12 that has a syringe barrel 14 defining a fluid chamber 16 and an elongated luer or tip 18 projecting from a distal end 20 of the syringe barrel 14. The luer 18 of the syringe 14 has a narrow passage 22 that extends through the luer and which communicates with the fluid chamber 16 of the syringe barrel 14. In the past the prior art syringes 12 have been manufactured from glass. Recently, however, more syringes 12 have been manufactured from suitable polymers.

The assignee of the present invention has filed application Ser. No. 09/801,864, which is incorporated herein by reference and made a part hereof, for a syringe produced from cyclic olefin containing polymers or bridged polycyclic hydrocarbon containing polymers. These polymers, in some instances, shall be collectively referred to as COCs. The presently preferred COC is a norbornene and ethylene copolymer. These norbornene copolymers are described in detail in U.S. Pat. Nos. 5,783,273, 5,744,664, 5,854,349, and 5,863,986. The norbornene ethylene copolymers preferably have from at least about 20 mole percent norbornene monomer and more preferably from about 20 mole percent to about 75 mole percent and most preferably from about 30 mole percent to about 60 mole percent norbornene monomer or any combination or subcombination of ranges therein. The norbornene ethylene copolymer should have a glass transition temperature of from about 70–180° C., more preferably from about 70–130° C. The heat deflection temperature at 0.45 Mpa should be from about 70° C. to about 200° C., more preferably from about 75° C. to about 150° C. and most preferably from about 76° C. to about 149° C. Also, in a preferred form of the invention, the COC is capable of withstanding, without significant heat distortion, sterilization by an autoclave process at 121° C. Suitable copolymers are sold by Ticona under the tradename TOPAS under grades 6013, 6015 and 8007 (not autoclavable). TOPAS is the preferred copolymer utilized in a preferred embodiment of the syringe body. Other suitable COCs are sold by Nippon Zeon under the tradename ZEONEX and ZEONOR, by Daikyo Gomu Seiko under the tradename CZ resin, and by Mitsui Petrochemical Company under the tradename APEL.

It has been found that the use of COC-based syringe bodies overcome many of the drawbacks associated with the use of glass syringe bodies. The biggest drawbacks of glass syringe bodies are in connection with the handling of the glass syringes. For instance, the glass syringes are often chipped, cracked, or broken during the manufacturing process. Glass particles may become trapped within the syringe bodies and subsequently sealed within the syringe barrel with the medical solution. This could be hazardous to a patient injected with the medical solution. Additionally, the glass particles could become a manufacturing hazard by causing injury to plant personnel or damage to expensive manufacturing equipment. While this specific syringe has been disclosed for illustrative purposes, one of ordinary skill in the art would understand that the tip cap 10 of the present invention would operate successfully with any type of syringe, whether made of glass, polymer or other material. Additionally, throughout this specification, syringes are used as an illustrative example of the type of container for which the tip cap is utilized, however, it should be understood that the tip cap of the present invention can be applied to any container, vial, other type of storage vessel, or IV kit without departing from the spirit of the invention.

The tip cap 10 of the present invention is removable secured to the tip 18 of the syringe 12 to maintain a sterile barrier for the syringe 12 when secured thereto, yet to additionally have acceptable removal forces during removal thereof. It is known that typical prior art tip caps, such as shown in FIG. 1, have undesirable localized contact pressures that result in undesirable removal forces. Typically, these prior art tip caps have undesirable localized contact pressures between the tip cap and the syringe luer adjacent the opening of the passage in the syringe luer. In some instances, these localized contact pressures at this point have led to a failure of the tip cap. Thus, it has been determined that both the material and geometry of the tip cap, as well as the mating luer, contribute to the contact and removal forces.

Additionally, while the removal forces and contact forces must be low enough such that the tip cap 10 is capable of being removed from the luer 18 without undesirable force required, the tip cap 10 must be capable of maintaining a secure seal with the luer 18 over an extended period of time, possibly including extended years of shelf-life.

As shown in FIGS. 4 and 5, the removable tip cap 10 of the present invention comprises a body having a proximal end 24 and a distal end 26, and an outer surface 28 and an inner surface 30. The inner surface 30 of the tip cap 10 extends into the body of the tip cap 10 at the proximal end 24 thereof to define a cavity 32. Annular ridges 34 protrude from the inner surface 30 and into the cavity 32 of the tip cap 10. As shown in FIG. 4, the annular ridges 34 may have a radius 35 at an edge thereof. The radius 35 on the annular ridges 34 assists in providing decreased removal forces for the tip cap 10. The radius 35 on the annular ridges 34 is adapted to deform against the surface variations of the luer 18 in order to provide a positive seal therewith. As such, the annular ridges 34 provide an interference fit for securing the tip cap 10 on the luer 18.

It should be understood that in the preferred embodiment the annular ridges 34 traverse a full 360° about the inner surface 30 of the cavity 32. Nevertheless, the annular ridges 34 may traverse about only a portion, or portions, of the inner surface 30 of the cavity 32. As one of ordinary skill in the art would understand, the annular ridges 34 may be provided as protrusions on the inner surface 30 of the cavity 32 to operate as contact areas 36 and to decrease the surface contact between the inner surface 30 of the tip cap 10 and the luer tip 18.

In the embodiment illustrated in FIG. 4, each of the plurality of adjacent annular ridges 34 extend from the inner surface 30 radially toward a centerline ($C_L$) of the tip cap 10. The annular ridges 34 define discrete contact areas 36 of the tip cap 10 (see FIG. 5) that engage the luer 18 of the syringe 12 when connected thereto. This modified contact area 36 of the tip cap 10 decreases the surface contact area between the inner surface 30 of the tip cap 10 and the syringe tip 18. Further, the contact pressure between the tip cap 10 and the luer tip 18 is significantly decreased at the distal end 40 of the cavity 32.

Additionally, the contact area 36 between the tip cap 10 and the syringe tip 18 provides an independent seal area to maintain a sterile barrier for the contents in the fluid chamber 16. When a plurality of annular ridges 34 are utilized, a plurality of independent and distinct seal areas are formed with the luer 18. In this embodiment, the seal areas as well as the contact areas 36 are annular. The seal area between the annular ridges 34 and the luer 18 provides an increased seal over prior art tip caps. While three adjacent annular ridges 34 are utilized in the preferred embodiment, it is understood that the use of one or more ridges 34 is acceptable without departing from the spirit of the invention.

The cavity 32 of the tip cap 10 also has a proximal end 38 and a distal end 40. The proximal end 38 of the cavity 32 is the substantially the same as the proximal end 24 of the tip cap 10. Additionally, in a preferred embodiment the cavity 32 of the tip cap 10 is frustoconical in shape, however, one of ordinary skill in the art would understand that other geometrical configurations of the cavity 32 may be possible without departing from the scope of the present invention. With such a configuration, each cross section of the cavity 32 has a diameter related therewith. As shown in FIG. 4, the proximal end 38 of the cavity 32 has a diameter $D_1$ (not referenced) that is larger than a diameter $D_2$ (not referenced) of the distal end 40 of the cavity 32. Additionally, as shown in FIG. 5, the diameter $D_1$ of the proximal end 38 of the cavity 32 is larger than a diameter $D_3$ (not referenced) of the syringe tip 18 adjacent the syringe barrel 14. Further as shown in FIG. 5, in this embodiment the diameter $D_2$ of the distal end 40 of the cavity 32 is larger than a diameter $D_4$ (not referenced) at an end of the syringe tip 18. Because of the annular ridges 34, the surface area of the frustoconical inner surface 30 is less than the surface area of the luer 18.

In a preferred embodiment, the diameter $D_1$ at the proximal end 38 of the cavity 32 is approximately 4.7 mm, the diameter $D_2$ at the distal end 40 of the cavity 32 is approximately 4.3 mm, and the diameter $D_4$ at the end of the syringe tip 18 is approximately 4.0 mm. Similarly, in a preferred embodiment, the diameter of the edge of the first annular ridge 34 adjacent the proximal end 38 of the cavity 32 is approximately 3.8 mm.

A protrusion 35 extends from the inner surface 30 of the tip cap 10 at the distal end 40 of the cavity 32. As shown in FIG. 6, when the tip cap 10 is mated with the luer 18, the protrusion 35 is adapted to extend into the narrow passage 22 that extends through the luer 18. Thus, the protrusion 35 operates as a seal for the passage 22 of the solution container 12.

Unlike other prior art tip caps, a preferred embodiment of the tip cap 10 of the present invention is manufactured as a unitary element and is made as a single integral component. In a preferred embodiment, the tip cap 10 is fabricated from a polymeric material. Suitable polymeric materials include, but are not limited to, synthetic rubbers including styrene-butadiene copolymer, acrylonitrile-butadiene copolymer, neoprene, butyl rubber, bromobutyl rubber, polysulfide elastomer, urethane rubbers, stereo rubbers, ethylene-propylene elastomers. Additionally, a teflon coating, or other similar coatings such as parylene, may be utilized to further reduce the material effect of the tip cap removal force. Furthermore, the tip cap 10 or the luer 18 may be siliconized. In a preferred form of the invention, the elastomeric component is a halogenated butyl rubber and more preferably a chlorobutyl-based elastomer. Additionally, the tip cap 10 is preferably made by an compression molding process.

With appropriate material and geometry combinations of the tip cap 10 and luer tip 18, during removal of the tip cap 10, the annular ridges 34 on the inner surface 30 will provide for incremental removal of the tip cap 10 from the luer tip 18. Under such an appropriate configuration, the annular ridges 34 result in incremental removal forces due to elongation of portions of the tip cap 10 during removal of the tip cap 10 from the luer 18. As such, rather than incurring a single large removal force during removal of the tip cap, and often a single large removal force due to a large contact pressure at the distal end 40 of the cavity, the annular ridges provide to distribute the removal force among both various portions of the tip cap 10 as well as incrementally about the removal process. As such, a single large contact pressure, and thus a single large removal force is not incurred, and the possibility of failure of the tip cap is significantly reduced and likely eliminated.

It will be understood that the invention may be embodied in other specific forms without departing from the spirit or central characteristics thereof. The present embodiments, therefore, are to be considered in all respects as illustrative and not restrictive, and the invention is not to be limited to the details given herein.

What is claimed is:

1. A removable tip cap fore syringe, the syringe having a syringe barrel defining a fluid chamber and an elongated tip projecting from a distal end of the syringe barrel, the tip defining a first diameter, wherein the tip has a narrow passage that extends therethrough and which communicates with the fluid chamber of the syringe barrel, the tip cap comprising:
    a body having an outer surface, a proximal end, a distal end, and a cavity extending into the body at the proximal end thereof, wherein an inner surface of the body defines the cavity and the cavity has a proximal end defining a second diameter and a distal end defining a third diameter, the second diameter of the proximal end of the cavity is larger than the third diameter of the distal end of the cavity and the third diameter of the distal end is larger than the first diameter of the syringe tip, the inner surface of the cavity having en annular ridge extending into the cavity and defining a contact area to engage the tip of the syringe, wherein the contact area of the annular ridge decreases a surface area of contact between the tip cap and the syringe tip, and wherein the annular ridge creates an annular seal with the syringe tip.

2. The removable tip cap of claim 1, wherein the body is a unitary element.

3. The removable tip cap of claim 1, wherein the body is made as a single component.

4. The removable tip cap of claim 1, further comprising a plurality of adjacent annular ridges on the inner surface of the tip cap.

5. The removable tip cap of claim 1, wherein the second diameter of the proximal end of the cavity is larger than a fifth diameter of the syringe tip adjacent the syringe barrel.

6. A removable tip cap for a luer of a polymeric medical solution container, comprising;
    an integral body having an outer portion and a cavity extending to an inner portion, the cavity having a frustoconical inner surface and an annular ring extending from the inner surface radially toward a centerline of the tip cap wherein the cavity has a proximal end, wherein a diameter defined at the proximal end of the cavity is larger than a diameter defined at the distal end of the cavity, and wherein the diameter of the distal end of the cavity is larger than a diameter defined at the end of the luer.

7. The removable tip cap of claim 6, wherein the annular ring has a radius at an edge thereof extending into the cavity, the radius of the annular ring adapted to contact and seal the tip cap against the luer.

8. The removable tip cap of claim 6, further comprising a plurality of annular rings extending radially toward a centerline of the tip cap from the frustoconical inner surface of the cavity.

9. The removable tip cap of claim 6, wherein the diameter of the proximal end of the cavity is larger than a diameter defined at a proximal end at the luer.

10. The removable tip cap of claim 6, wherein the body is integrally formed of a thermoplastic elastomer.

11. The removable tip cap of claim 6, wherein the body is integrally formed of rubber component.

12. The removable tip cap of claim 6, wherein the body is integrally formed of chlorobutyl rubber component.

13. A removable tip cap for an elongated luer tip projecting from a distal end of a fluid chamber, wherein the luer tip has a narrow passage that extends therethrough and which communicates with the fluid chamber, the tip cap comprising:
    an integral body having an outer surface, a proximal end, a distal end, and a cavity extending into the body at the proximal end thereof, wherein an inner surface of the body defines the cavity and has a plurality of adjacent annular ridges extending radially toward a centerline of the body, the annular ridges defining contact areas adapted to engage the luer tip, the contact areas decreasing the area of contact area between the tip cap and the luer tip, and the annular ridges creating annular seals with the luer tip, and wherein the cavity has a proximal end and a distal end, wherein a diameter of the proximal end of the cavity is larger than a diameter of the distal end of the cavity, and wherein the diameter of the distal end of the cavity is larger than a diameter at the end of the luer tip.

14. The removable tip cap of claim 13, wherein the inner surface of the body is frustoconical in shape.

15. The removable tip cap of claim 13, wherein a termination of the annular ridges has a radius, the radius adapted to deform against the luer tip to seal the tip cap against the luer tip.

16. The removable tip cap of claim 13, wherein each of the plurality of annular ridges defines an independent seal area with the luer tip.

17. The removable tip cap of claim 16, wherein the tip cap has a plurality of independent seal areas.

18. The removable tip cap of claim 13, wherein each of the plurality of annular ridges defines a distinct seal area between the tip cap and the luer tip.

19. The removable tip cap of claim 13, wherein the diameter of the proximal end of the cavity is larger than a diameter of the luer tip adjacent the container.

20. A syringe assembly comprising:

a syringe having a syringe barrel defining a fluid chamber and an elongated tip projecting from a distal end of the syringe barrel, wherein the tip has a narrow passage that extends therethrough and which communicates with the fluid chamber of the syringe barrel; and, a removable tip cap for the syringe, the tip cap having an integral body having an outer surface, a proximal end, a distal end, and a cavity extending into the body at the proximal end thereof, the cavity having a frustoconical inner surface and at least one annular ridge extending from the inner surface radially toward a centerline of the tip cap, the annular ridge defining a contact area adapted to engage the tip of the syringe, the contact area decreasing a surface area of contact between the tip cap and the tip of the syringe, and the annular ridge providing an annular seal with the tip wherein a diameter at the distal end of the cavity is larger than a diameter at a distal end of the syringe tip.

21. The syringe assembly of claim 20, wherein the tip cap has a plurality of adjacent annular ridges, each of the annular ridges extending radially toward a centerline of the body, the annular ridges defining contact areas adapted to engage the tip of the syringe, the contact areas decreasing the surface area of contact between the tip cap and the tip at the syringe.

22. The syringe assembly of claim 21, wherein each of the plurality of annular ridges defines an independent seal area with the tip of the syringe.

23. The syringe assembly of claim 20, wherein a diameter at the proximal end of the cavity is larger then a diameter of the syringe tip adjacent the syringe barrel.

24. The syringe assembly of claim 20, wherein the annular ring has a radius at an edge thereof extending into the cavity, the radius of the annular ring adapted to contact and seal the tip cap against the tip of the syringe.

* * * * *